United States Patent
Hanley et al.

(10) Patent No.: US 8,425,500 B2
(45) Date of Patent: Apr. 23, 2013

(54) METHOD AND APPARATUS FOR PROTECTING CAPILLARY OF LASER FIBER DURING INSERTION AND REDUCING METAL CAP DEGRADATION

(75) Inventors: Brian Hanley, Framingham, MA (US); Jessica Hixon, Watertown, MA (US); Alfred Intoccia, Nashua, NH (US); Christopher L. Oskin, Grafton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1009 days.

(21) Appl. No.: 12/468,634

(22) Filed: May 19, 2009

(65) Prior Publication Data

US 2010/0016845 A1  Jan. 21, 2010

Related U.S. Application Data

(60) Provisional application No. 61/054,281, filed on May 19, 2008.

(51) Int. Cl.
*A61B 18/22* (2006.01)

(52) U.S. Cl.
USPC ............................................ 606/15; 29/426.2

(58) Field of Classification Search ................ 606/1–19; 607/88–94; 128/898; 385/75–77, 94
See application file for complete search history.

(56) References Cited

U.S. PATENT DOCUMENTS

| | | | |
|---|---|---|---|
| 4,507,652 A | 3/1985 | Vogt et al. | |
| 4,740,047 A | 4/1988 | Abe et al. | |
| 5,000,537 A | 3/1991 | Saito et al. | |
| 5,257,991 A | 11/1993 | Fletcher et al. | |
| 5,283,850 A | 2/1994 | Souloumiac | |
| 5,343,543 A | 8/1994 | Novak, Jr. et al. | |
| 5,357,955 A | 10/1994 | Wolf et al. | |
| 5,409,483 A | 4/1995 | Campbell et al. | |
| 5,486,171 A * | 1/1996 | Chou | 606/16 |
| 5,495,541 A | 2/1996 | Murray | |
| 5,509,917 A | 4/1996 | Cecchetti et al. | |
| 5,562,657 A | 10/1996 | Griffin | |
| 5,571,099 A | 11/1996 | Purcell, Jr. et al. | |
| 5,638,483 A | 6/1997 | Konwitz | |
| 5,772,657 A | 6/1998 | Hmelar et al. | |
| 5,993,380 A | 11/1999 | Yabe et al. | |
| 6,296,608 B1 | 10/2001 | Daniels et al. | |
| 6,454,471 B1 | 9/2002 | Ware et al. | |
| 6,615,072 B1 | 9/2003 | Izatt et al. | |

(Continued)

*Primary Examiner* — Sam Yao
*Assistant Examiner* — John W Hall
(74) *Attorney, Agent, or Firm* — Bookoff McAndrews, PLLC

(57) ABSTRACT

A method and an apparatus according to an embodiment of the invention includes disposing a cover about a capillary used in a side-firing optical fiber. The cover can be used to protect the capillary when being inserted through an endoscope for medical treatment. In some embodiments, the cover can be a low-profile cover such as a coating made of a light-sensitive polymer or like material. At least a portion of the coating can be removed after insertion by exposing the light-sensitive material to laser energy transmitted from an optical-fiber-core end housed within the capillary. In other embodiments, the cover can be a slideable or moveable low-profile sleeve or metal cover. During insertion, the sleeve or metal cover is positioned over the capillary. After insertion, the sleeve or metal cover is retracted to expose the area to be treated to side-fired laser energy transmitted from the capillary.

7 Claims, 12 Drawing Sheets

U.S. PATENT DOCUMENTS

| | | |
|---|---|---|
| 6,616,462 B2 | 9/2003 | Saitoh |
| 6,928,202 B2 | 8/2005 | Pickrell et al. |
| 7,169,140 B1 | 1/2007 | Kume |
| 7,207,980 B2 | 4/2007 | Christian et al. |
| 7,274,843 B2 | 9/2007 | James, IV et al. |
| 2005/0203419 A1 | 9/2005 | Ramanujam et al. |
| 2006/0078265 A1 | 4/2006 | Loeb |
| 2007/0106286 A1 | 5/2007 | Harschack et al. |
| 2007/0179485 A1 | 8/2007 | Yeik et al. |
| 2010/0198009 A1 | 8/2010 | Farr et al. |

* cited by examiner

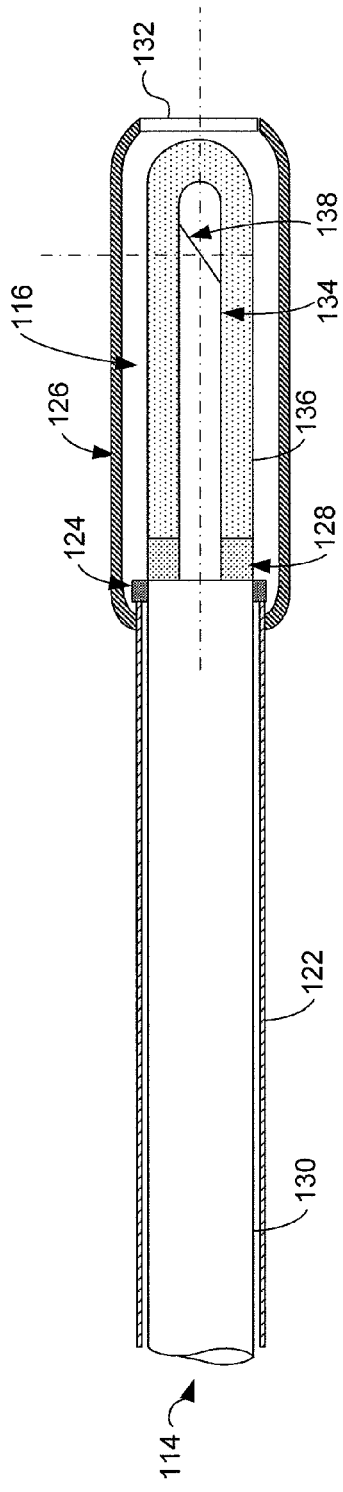
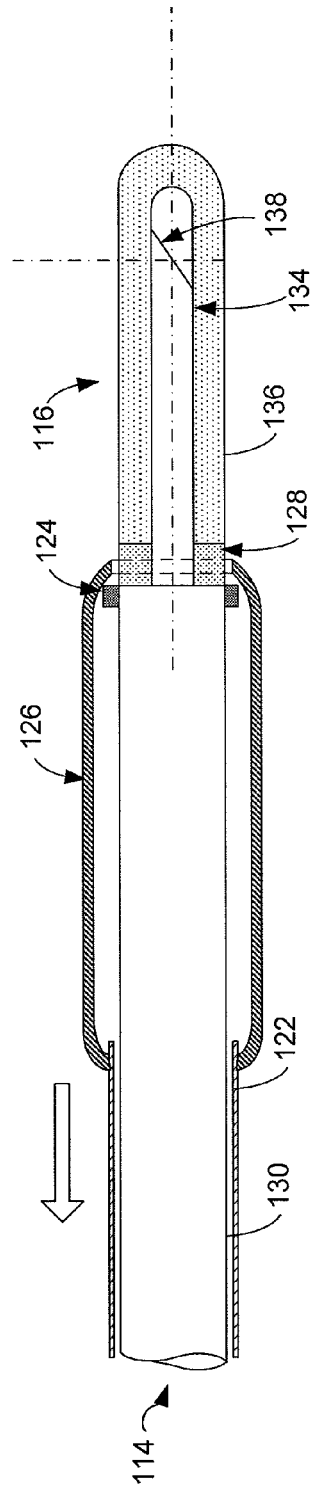

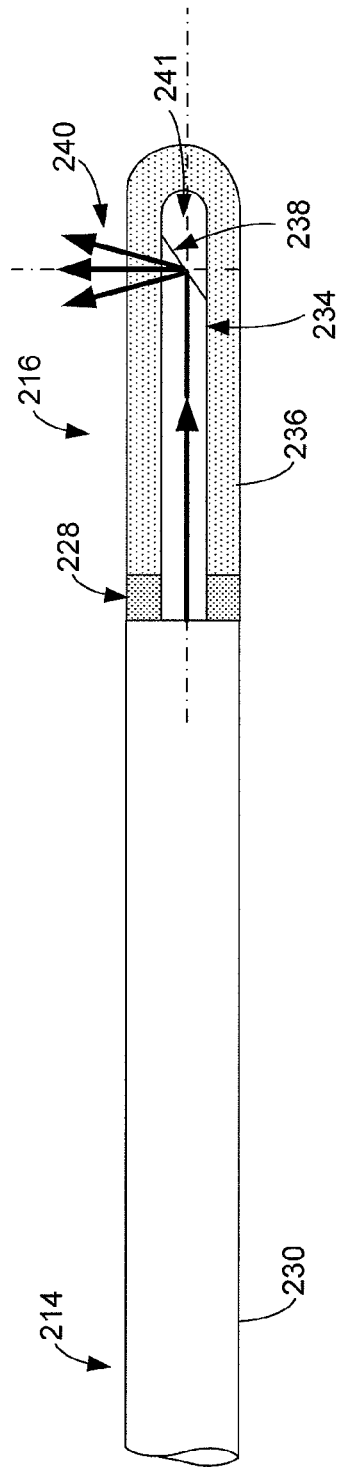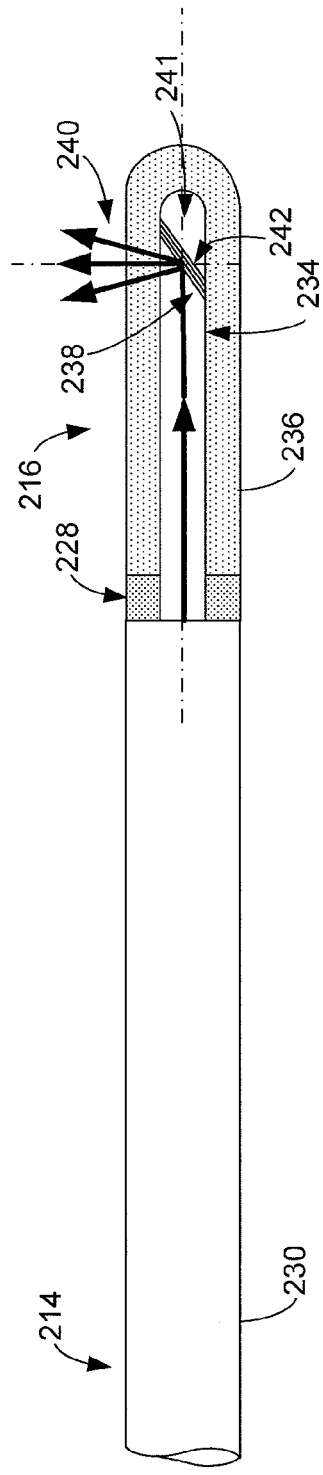
FIG. 4A
FIG. 4B

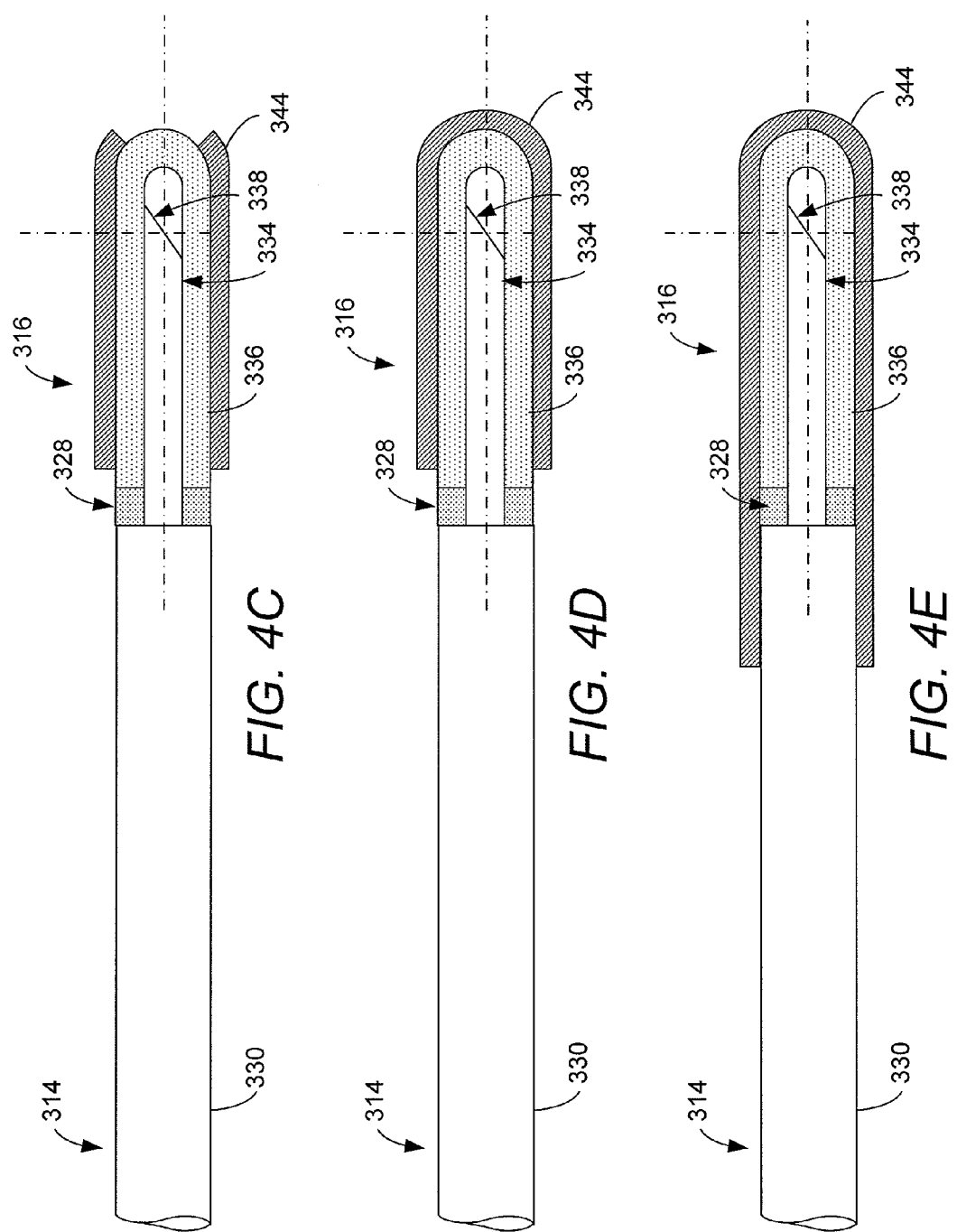

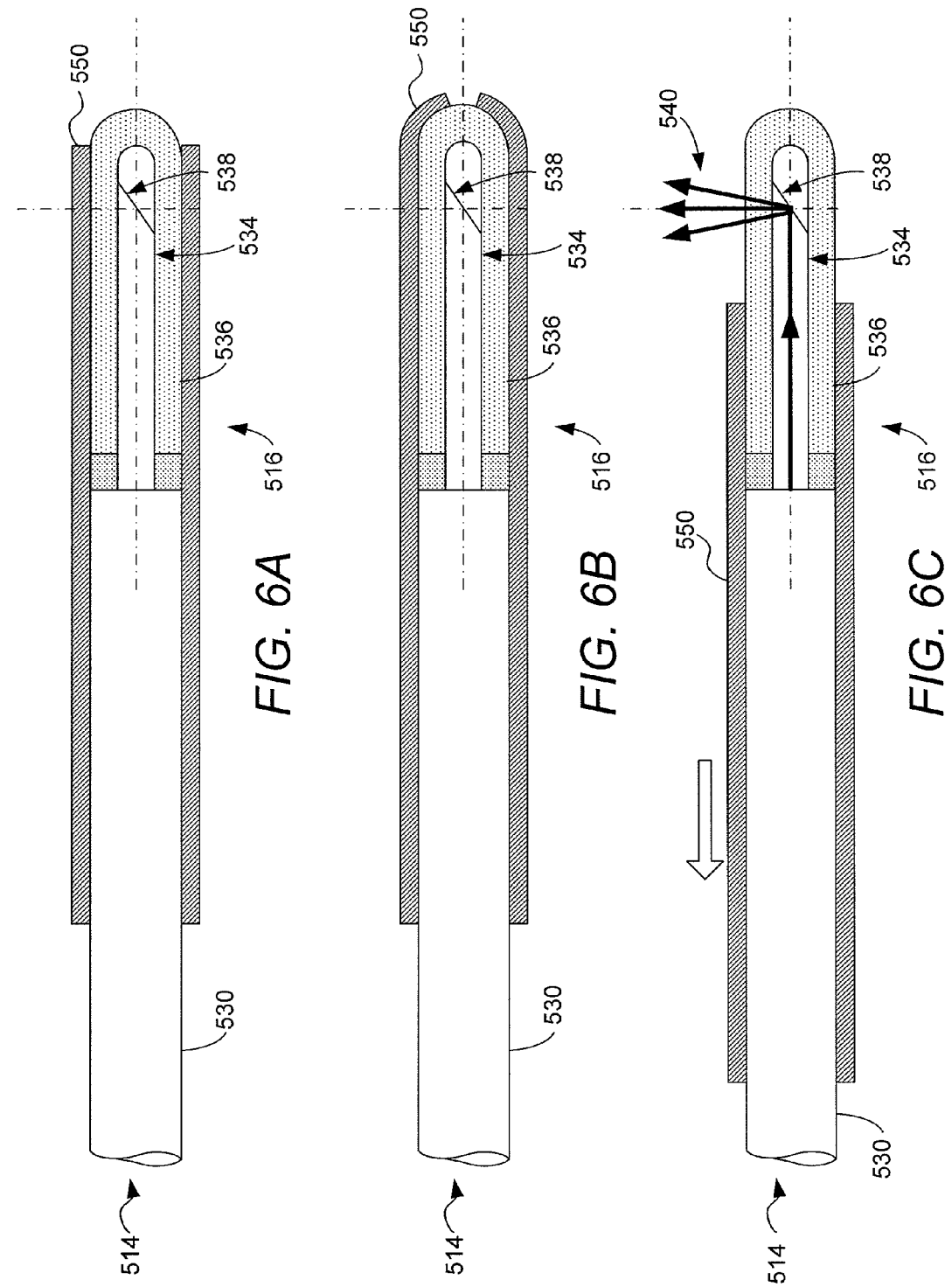

METHOD AND APPARATUS FOR PROTECTING CAPILLARY OF LASER FIBER DURING INSERTION AND REDUCING METAL CAP DEGRADATION

RELATED APPLICATION

This application claims priority to and the benefit of U.S. Provisional Application No. 61/054,281, filed on May 19, 2008, entitled "Method and Apparatus for Protecting Capillary of Laser Fiber During Insertion and Reducing Metal Cap Degradation," which is incorporated herein by reference in its entirety.

BACKGROUND

The invention relates generally to medical devices and more particularly to side-firing optical fibers and methods for using such devices.

By using side-firing or laterally-firing optical fibers for laser-based surgical procedures, a medical practitioner can more accurately control the application of laser energy to the appropriate treatment area. Passing the distal end portion of the optical fiber through an endoscope during surgery, however, may damage, scratch, degrade, or deform the distal end portion of the optical fiber. A damaged optical-fiber end portion may reduce side-firing laser energy delivered or increase overheating during use of the device. To protect the optical-fiber end portion, a metal cap, tube, or cannula, usually made of surgical grade stainless steel, is placed over the optical fiber end. In some instances, using a protective metal cap increases the profile or size of the optical fiber end for insertion and positioning within the endoscope.

Another consideration in laser-based surgical procedures is the effect of back-scattered laser energy during treatment. When sufficient back-scattered laser energy strikes a protective metal cap, the protective metal cap can also degrade and portions can be released into the patient's body. Moreover, an overheated protective metal cap can also affect the mechanical and optical properties of those portions of the optical fiber end that are in close proximity. Cooling of the device may be needed to operate at a safe temperature.

Thus, a need exists for optical fiber end portions that can increase side-fired laser energy, increase device longevity, increase transmission efficiency, reduce overheating, and/or increase patient safety.

SUMMARY

A method and an apparatus according to an embodiment of the invention includes disposing a cover about a capillary used in a side-firing optical fiber. The cover can be used to protect the capillary when being inserted through an endoscope for medical treatment. In some embodiments, the cover can be a low-profile cover such as a coating made of a light-sensitive polymer or like material. At least a portion of the coating can be removed after insertion by exposing the light-sensitive material to laser energy transmitted from an optical-fiber-core end housed within the capillary. In other embodiments, the cover can be a slideable or moveable low-profile sleeve or metal cover. During insertion, the sleeve or metal cover is positioned over the capillary. After insertion, the sleeve or metal cover is retracted to expose the area to be treated to side-fired laser energy transmitted from the capillary.

BRIEF DESCRIPTION OF THE DRAWINGS

FIGS. 3A-3B are cross-sectional views of an optical-fiber distal end portion with a protective metal cap, according to an embodiment.

FIG. 4A is a cross-sectional view of an optical-fiber distal end portion with a core-end angled surface disposed within a capillary, according to an embodiment.

FIG. 4B is a cross-sectional view of an optical-fiber distal end portion with a core-end angled surface and multilayer dielectric coating disposed within a capillary, according to an embodiment.

FIGS. 4C-4E are cross-sectional views of a capillary with a low-profile coating according to an embodiment.

FIGS. 6A-6C are cross-sectional views of a capillary with a low-profile sleeve according to an embodiment.

DETAILED DESCRIPTION

Figure 1:
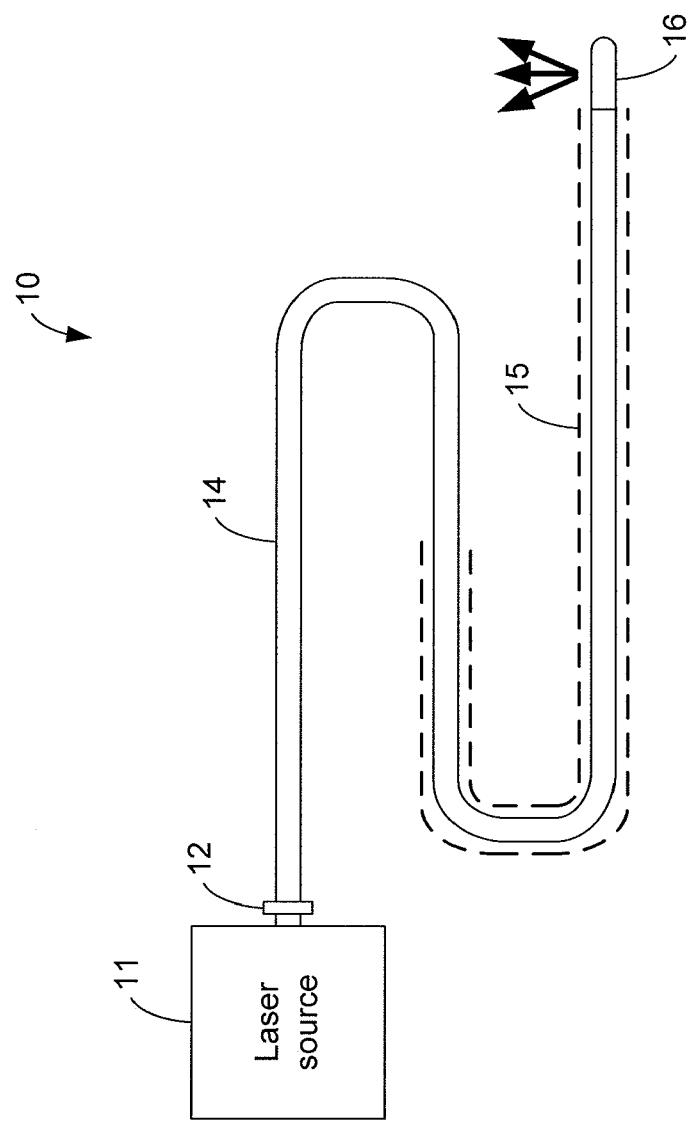
FIG. 1 is a schematic representation of a side-firing optical fiber system according to an embodiment.

The devices and methods described herein are generally related to the use of side-firing optical fibers within the body of a patient. For example, the devices and methods are suitable for use in treating symptoms related to an enlarged prostate gland, a condition known as Benign Prostatic Hyperplasia (BPH). BPH is a common condition in which the prostate becomes enlarged with aging. The prostate is a gland that is part of the male reproductive system. The prostate gland includes two lobes that are enclosed by an outer layer of tissue and is located below the bladder and surrounding the urethra, the canal through which urine passes out of the body. Prostate growth can occur in different types of tissue and can affect men differently. As a result of these differences, treatment varies in each case. No cure for BPH exists and once the prostate begins to enlarge, it often continues, unless medical treatment is initiated.

Patients who develop symptoms associated with BPH generally need some form of treatment. When the prostate gland is mildly enlarged, research studies indicate that early treatment may not be needed because the symptoms clear up without treatment in as many as one-third of cases. Instead of immediate treatment, regular checkups are recommended. Only if the condition presents a health risk or the symptoms result in major discomfort or inconvenience to the patient is treatment generally recommended. Current forms of treatment include drug treatment, minimally-invasive therapy, and surgical treatment. Drug treatment is not effective in all cases and a number of procedures have been developed to relieve BPH symptoms that are less invasive than conventional surgery.

While drug treatments and minimally-invasive procedures have proven helpful for some patients, many doctors still recommend surgical removal of the enlarged part of the prostate as the most appropriate long-term solution for patients with BPH. For the majority of cases that require surgery, a procedure known as Transurethral Resection of the Prostate (TURP) is used to relieve BPH symptoms. In this procedure, the medical practitioner inserts an instrument called a resectoscope into and through the urethra to remove the obstructing tissue. The resectoscope also provides irrigating fluids that carry away the removed tissue to the bladder.

More recently, laser-based surgical procedures employing side-firing optical fibers and high-power lasers have been used to remove obstructing prostate tissue. In these procedures, a doctor passes the optical fiber through the urethra using a cystoscope, a specialized endoscope with a small camera on the end, and then delivers multiple bursts of laser energy to destroy some of the enlarged prostate tissue and to shrink the size of the prostate. Patients who undergo laser surgery usually do not require overnight hospitalization and in most cases the catheter is removed the same day or the morning following the procedure. Generally, less bleeding occurs with laser surgery and recovery times tend to be shorter than those of traditional procedures such as TURP surgery.

A common laser-based surgical procedure is Holmium Laser Enucleation of the Prostate (HoLEP). In this procedure, a holmium:YAG (Ho:YAG) laser is used to remove obstructive prostate tissue. The Ho:YAG surgical laser is a solid-state, pulsed laser that emits light at a wavelength of approximately 2100 nm. This wavelength of light is particularly useful for tissue ablation as it is strongly absorbed by water. An advantage of Ho:YAG lasers is that they can be used for both tissue cutting and for coagulation. Another common laser surgery procedure is Holmium Laser Ablation of the Prostate (HoLAP), where a Ho:YAG laser is used to vaporize obstructive prostate tissue. The decision whether to use HoLAP or HoLEP is based primarily on the size of the prostate. For example, ablation may be preferred when the prostate is smaller than 60 cc (cubic centimeters). Laser-based surgical procedures, such as HoLAP and HoLEP, are becoming more preferable because they produce similar results to those obtained from TURP surgery while having fewer complications and requiring shorter hospital stay, shorter catheterization time, and shorter recovery time.

An optical fiber system as described herein can be used to transmit laser energy from a laser source to a target treatment area within a patient's body. The optical fiber system can include a laser source and an optical fiber. One end of the optical fiber can be coupled to the laser source while the other end of the optical fiber, the distal end portion (e.g., the end with a side-firing or laterally-firing portion), can be inserted into the patient's body to provide laser treatment. The distal end portion can include a capillary and a low-profile cover over the capillary. In some embodiments, an angled or beveled end surface of the optical fiber core disposed within the capillary can redirect laser energy in a lateral direction for side-firing transmission of laser energy to the area of treatment. The angled end surface of the core can include, for example, a multilayer dielectric coating. The multilayer dielectric coating can be configured to reflect a portion of the optical beam (e.g., laser beam) that impinges on the end surface of the core at a less glancing angle and would not otherwise be =totally internally reflected. In one embodiment, the low-profile cover can include a coating positioned over or deposited onto at least a portion of the capillary. In another embodiment, the low-profile cover can include a slideable or moveable sleeve that is positioned over at least a portion of the capillary. In some embodiments, the capillary can be a multi-capillary.

It is noted that, as used in this written description and the appended claims, the singular forms "a," "an" and "the" include plural referents unless the context clearly dictates otherwise. Thus, for example, the term "a wavelength" is intended to mean a single wavelength or a combination of wavelengths. Furthermore, the words "proximal" and "distal" refer to direction closer to and away from, respectively, an operator (e.g., medical practitioner, medical practitioner, nurse, technician, etc.) who would insert the medical device into the patient, with the tip-end (i.e., distal end) of the device inserted inside a patient's body. Thus, for example, the optical fiber end inserted inside a patient's body would be the distal end of the optical fiber, while the optical fiber end outside a patient's body would be the proximal end of the optical fiber.

FIG. 1 is a schematic representation of a side-firing optical fiber system according to an embodiment of the invention. An optical fiber side-firing system 10 can include a laser source 11, an optical coupler 12, an optical fiber 14, and an optical-fiber distal end portion 16. The optical fiber side-firing system 10 also includes a suitable catheter or endoscope 15 for inserting the optical-fiber distal end portion 16 into a patient's body. The laser source 11 can include at least one laser that can be used for generating laser energy for surgical procedures. The laser source 11 can include a Ho:YAG laser, for example. The laser source 11 can include at least one of a neodymium-doped:YAG (Nd:YAG) laser, a semiconductor laser diode, or a potassium-titanyl phosphate crystal (KTP) laser, for other examples. In some embodiments, more than one laser can be included in the laser source 11 and more than one laser can be used during a surgical procedure. The laser source 11 can also have a processor that provides timing, wavelength, and/or power control of the laser. For example, the laser source 11 can include mechanisms for laser selection, filtering, temperature compensation, and/or Q-switching operations.

The optical fiber 14 can be coupled to the laser source 11 through the optical coupler 12. The optical coupler 12 can be an SMA connector, for example. The proximal end of the optical fiber 14 can be configured to receive laser energy from the laser source 11 and the distal end of the optical fiber 14 can be configured to output the laser energy through the optical-fiber distal end portion 16. The optical fiber 14 can include, for example, a core, one or more cladding layers about the core, a buffer layer about the cladding, and a jacket. The core can be made of a suitable material for the transmission of laser energy from the laser source 11. In some embodiments, when surgical procedures use wavelengths ranging from about 500 nm to about 2100 nm, the core can be made of silica with a low hydroxyl ($OH^-$) ion residual concentration An example of using low-hydroxyl (low-OH) fibers in medical devices is described in U.S. Pat. No. 7,169,140 to Kume, the disclosure of which is incorporated herein by reference in its entirety. The core can be multi-mode and can have a step or graded index profile. The cladding can be a single or a double cladding that can be made of a hard polymer or silica. The buffer can be made of a hard polymer such as Tefzel®, for example. When the optical fiber includes a jacket, the jacket can be made of Tefzel®, for example, or can be made of other polymers.

The endoscope 15 can define one or more lumens. In some embodiments, the endoscope 15 includes a single lumen that can receive therethrough various components such as the optical fiber 14. The endoscope 15 has a proximal end configured to receive the optical-fiber distal end portion 16 and a distal end configured to be inserted into a patient's body for positioning the optical-fiber distal end portion 16 in an appropriate location for a laser-based surgical procedure. For example, to relieve symptoms associated with BPH, the endoscope 15 can be used to place the optical-fiber distal end portion 16 at or near the enlarged portion of the prostate gland. The endoscope 15 includes an elongate portion that can be flexible to allow the elongate portion to be maneuvered within the body. The endoscope 15 can also be configured to receive various medical devices or tools through one or more lumens of the endoscope, such as, for example, irrigation and/or suction devices, forceps, drills, snares, needles, etc. An example of such an endoscope with multiple lumens is described in U.S. Pat. No. 6,296,608 to Daniels et, al., the disclosure of which is incorporated herein by reference in its entirety. In some embodiments, a fluid channel (not shown) is defined by the endoscope 15 and coupled at a proximal end to a fluid source (not shown). The fluid channel can be used to irrigate an interior of the patient's body during a laser-based surgical procedure. In some embodiments, an eyepiece (not shown) can be coupled to a proximal end portion of the endoscope 15, for example, and coupled to an optical fiber that can be disposed within a lumen of the endoscope 15. Such an embodiment allows a medical practitioner to view the interior of a patient's body through the eyepiece.

The optical-fiber distal end portion 16 can include one or more members, elements, or components that can individually or collectively operate to transmit laser energy in a lateral direction offset from a longitudinal axis or centerline of the distal end of the optical fiber core. In an embodiment, the optical-fiber distal end portion 16 can have a protective low-profile cover that includes a coating made of a light-sensitive material. In another embodiment, the optical-fiber distal end portion 16 can have a protective low-profile cover that includes a slideable sleeve or tubing than can be retracted to expose the optical-fiber distal end portion 16 to a treatment area during a surgical procedure.

Figure 2:
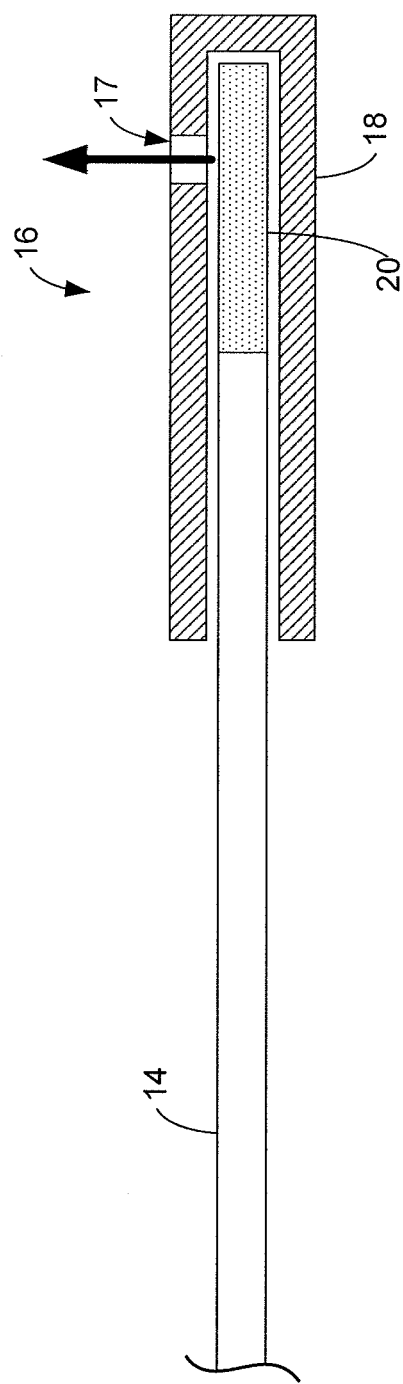
FIG. 2 is a cross-sectional view of an optical-fiber distal end portion according to an embodiment.

FIG. 2 is a cross-sectional view of the optical-fiber distal end portion 16, according to an embodiment of the invention. The optical-fiber distal end portion 16 can include an inner portion 20 and surrounded by an outer portion 18. The outer portion 18 can include, for example, a metal or ceramic cover or cap. The cover or cap is generally made of surgical grade stainless steel or other materials with like properties. In some instances, it can be desirable to have the cap made of a ceramic material (e.g., alumina) because certain ceramics can offer stable characteristics at high-temperatures and/or have a high reflectance value at the laser operating wavelength. The outer portion 18 can provide protection to the optical-fiber distal end portion 16. In one embodiment, the outer portion 18 can include a low-profile coating made of a light-sensitive material. In another embodiment, the outer portion 18 can define a low-profile sleeve or tubing that is slideable relative to the inner portion 20 and/or the optical-fiber distal end portion 16. In some embodiments, the outer portion 18 may be a low-profile coating or sleeve instead of a metal cap or other a high-profile member.

The outer portion 18 can include a window or transmissive portion 17 through which laterally-redirected or side-fired laser energy can be transmitted for surgical treatment. For example, when the outer portion 18 is made of an opaque material, a window can be defined after removing at least a portion of the opaque material. In another example, when the outer portion 18 is made of an optically-transmissive material, laser energy can be transmitted or sent through the outer portion 18. In some embodiments, the optically-transmissive material can be treated thermally, optically, mechanically, and/or chemically to improve its structural and/or optical characteristics such that laser energy can be delivered more effectively to the target area. For example, the optically-transmissive material can be thermally treated during manufacturing using a $CO_2$ laser.

The inner portion 20 can include one or more members, components, and/or devices to redirect laser energy. For example, the inner portion 20 can include a capillary or capillary tube. The capillary can be made of, for example, at least one of silica, sapphire, and/or other like materials. In one embodiment, the inner portion 20 can include a distal end portion of the core of the optical fiber 14 disposed within a capillary. As described below in more detail, the inner portion 20 can also include reflecting members and/or mirrors that can be used to redirect laser energy to provide side-firing operations.

FIGS. 3A-3B illustrate a cross-sectional view of an optical-fiber distal end portion 116 with a slideable protective metal cap. The optical-fiber distal end portion 116 can include a capillary 136, an optical-fiber-core end portion 134, and a fusion region 128. The optical-fiber-core end portion 134 can be disposed within a region defined inside the capillary 136. The optical-fiber-core end portion 134 can include a core-end angled surface 138 that is angled or beveled relative to a longitudinal axis or centerline of the optical-fiber-core end portion 134. The core-end angled surface 138 can be configured such that the angled surface produces reflection of laser energy that is transmitted through the optical-fiber-core end portion 134 to laterally redirect the laser energy. The core-end angled surface 138 can be used to redirect laser energy in a lateral direction offset from a longitudinal axis or centerline of the optical-fiber-core end portion 134.

In some embodiments, a proximal end portion of the capillary 136 can be coupled to a distal end portion of a cladding layer (not shown in FIGS. 3A-3B) and/or a distal end portion of a buffer layer 130 of an optical fiber 114 through a fusion process that produces an interface or fusion region 128. For example, a $CO_2$ laser can be used during manufacturing to perform the fusion operation. In some embodiments, to minimize laser energy reflections that can occur between the optical fiber 114 and the capillary 136, the refractive indices of the buffer layer 130 and/or the cladding layer of the optical fiber 114 can be substantially matched to the refractive index of the capillary 136. Reducing or minimizing the formation of bubbles, air gaps, and/or defects at the fusion region 128 during the fusion process can also minimize interface reflections. The cladding and/or buffer layer $OH^-$ ion concentration can also be controlled to match that of the capillary 136. Matching refractive indices can improve the mechanical and/or optical integrity of the fusion region 128 by minimizing thermal behavior differences between the distal end portion of the optical fiber 114 and the capillary 136.

As shown in FIG. 3A, a protective metal cap 126 can be disposed about the optical-fiber distal end portion 116. The protective metal cap 126 can include an opening 132 that can be configured to enable the protective metal cap 126 to move or slide about the optical-fiber distal end portion 116 and/or a portion of the optical fiber 114. The opening 132 can be defined at the distal end of the protective metal cap 126. The protective metal cap 126 can be made of, for example, surgical grade stainless steel or other like materials. A proximal end portion of the protective metal cap 126 can be coupled to a distal end portion of a retractable tubing 122 disposed about the buffer layer 130. The retractable tubing 122 can define a tubing or sleeve that can be configured to slide or move relative to the buffer layer 130. The retractable tubing 122 can be made of, for example, a polymer, a plastic, and/or other like material.

As shown in FIG. 3A, the protective metal cap 126 can be in a first position when the optical-fiber distal end portion 116 is covered by the protective metal cap 126. A positive stop 124 (e.g., a lip, a protrusion, a projection) can be disposed on the optical fiber 114. The positive stop 124 can be configured to define the placement or positioning of the protective metal cap 126 over the capillary 136 while in the first position. In this regard, the positive stop 124 can be used to limit the retractable tubing 122 coupled to the protective metal cap 126 from sliding in a distal direction beyond the location of the positive stop 124.

As shown in FIG. 3B, the protective metal cap 126 can be in a second or subsequent position to expose the optical-fiber distal end portion 116 for side-firing operations related to surgical treatment. For example, the distal end portion of the retractable tubing 122 can slide or move in a proximal direction and away from the positive stop 124 such that the protective metal cap 126 can slide relative to the optical-fiber distal end portion 116. In this regard, the positive stop 124 can be configured to limit the placement or positioning of the protective metal cap 126 while in the second or subsequent position. For example, the positive stop 124 can be used to limit the distal end portion of the protective metal cap 126 from sliding in a proximal direction beyond the location of the positive stop 124. During the sliding of the protective metal cap 126, the optical-fiber distal end portion 116 can pass through the opening 132. The protective metal cap 126 is generally configured to have a sufficiently high profile to allow the optical-fiber distal end portion 116 to slide through the opening 132 without damaging, scratching, and/or affecting the optical-fiber distal end portion 116.

In another embodiment, the opening 132 can be configured to enable laser energy transmitted through a portion of the capillary 136 to be transmitted through the opening 132. In this regard, the opening 132 can be defined offset from a longitudinal axis or centerline of the optical-fiber-core end portion 134. The protective metal cap 126 can be in a first position when a solid portion of the protective metal cap 126 is covering a portion of the capillary 136 through which the laterally-redirected laser energy is transmitted. The protective metal cap 126 can be in a second or subsequent position when the opening 132 at least partially aligns with the portion of the capillary 136 through which the laterally-redirected laser energy is transmitted such that the laser energy be transmitted through the opening 132.

FIGS. 4A-4B illustrate a cross-sectional view of an optical-fiber distal end portion 216 with a core-end angled surface 238 disposed within a capillary 236, according to embodiments of the invention. The capillary 236 that can be configured to receive an optical-fiber-core end portion 234. For example, a region can be defined within the capillary 236 that is configured to receive the optical-fiber-core end portion 234. As shown in FIG. 4A, the optical-fiber-core end portion 234 can include a core-end angled surface 238 that is angled or beveled relative to a longitudinal axis or centerline of the optical-fiber-core end portion 234. The core-end angled surface 238 can be polished such that the appropriate angle is achieved. The core-end angled surface 238 can be configured such that the angled surface produces reflection of laser energy that is transmitted through the optical-fiber-core end portion 234 to laterally redirect or side-fire the laser energy.

The angle of the core-end angled surface 238 can be determined based on at least one of several parameters. For example, the angle can be configured based on the wavelength of a laser energy 240, the exit or output location for the side-fired laser energy, and/or the optical properties of the optical-fiber-core end portion 234 and/or the capillary 236. Moreover, the optical properties of a region 241, located between the core-end angled surface 238 and the inner portion of the distal end of the capillary 236, can also be used in determining an appropriate angle for the core-end angled surface 238. By determining an appropriate angle for the core-end angled surface 238, the side-fired laser energy 240 can be transmitted in a lateral direction that is appropriate for laser-based surgical procedures.

In some instances, some of the laser energy transmitted through the optical-fiber-core end portion 234 is not laterally reflected at the core-end angled surface 238 and instead it is transmitted to the region 241 and then through the distal end of the capillary 236. This leakage laser energy is thus transmitted in a direction that is substantially parallel to the optical-fiber distal end portion 216 and not in a side-fired or laterally-redirected direction. To minimize the amount of laser energy that is leaked in this manner, the core-end angled surface 238 can also include a reflective coating that operates collectively with the angle of incidence of the laser energy to increase the efficiency with which the laser energy transmitted through the optical-fiber-core end portion 234 is laterally redirected for side-firing operations.

As shown in FIG. 4B, the core-end angled surface 238 can include a multilayer dielectric coating 242. The multilayer dielectric coating 242 can be made of a plurality of dielectric layers that collectively and efficiently operate to reflect laser energy. A dielectric layer can be made of alternating layers of $SiO_2$ (silica) and $TiO_2$ (titanium dioxide or titania), for example. The multilayer dielectric coating 242 can include alternating layers of two or more materials each with a different dielectric constant. In some embodiments, the multilayer dielectric coating 242 can be configured to operate as a ¼ wavelength mirror in which sets of two alternating layers are used and each layer has an optical thickness that is ¼ the wavelength of the laser energy. The multilayer dielectric material 242 can be deposited on the core-end angled surface 238 by using any of multiple deposition techniques, such as electron beam or ion beam deposition, for example.

The multilayer dielectric coating 242 can be used to improve the reflection efficiency of the core-end angled surface 238 when compared to other types of coated components, such as metallic mirrors or metallic coated glass mirrors, for example. The high reflectivity and low optical absorption of multilayer dielectric coatings can reduce the device operating temperature and/or reduce the amount of cooling that may be used to operate the device at a safe temperature.

FIGS. 4C-4E illustrate a cross-sectional view of a capillary 336 with a low-profile coating 344, according to embodiments of the invention. The low-profile coating 344 can be disposed on at least a portion of an outer surface of the capillary 336. In some embodiments, the low-profile coating 344 can be made of a material that is optically opaque to the laser energy that is used by the optical fiber side-firing system. The low-profile coating 344 can include a light-sensitive material such that, when exposed to laser energy, the material can be removed or dissolved. For example, the light-sensitive material can include a polymer having particles and/or other materials that sensitize the polymer to the wavelength of the laser energy used by the optical fiber side-firing system. The sensitized polymer can then be ablated or removed through a photothermal and/or a photochemical mechanism when exposed to the laser energy. In some embodiments, the low-profile coating 344 can include a material that can become light-sensitive through a chemical, optical, and/or thermal process after the material has been disposed on the outer surface of the capillary 336. The low-profile coating 344 can be made of a material that is sensitive to a wavelength of laser energy and/or an amount or dose of laser energy. For example, the low-profile coating 344 can be made of a material that is sensitive to a wavelength and/or a dose of a laser energy that is used by the optical fiber side-firing system.

The low-profile coating 344 can be deposited on at least a portion of the outer surface of the capillary 336 by using any of multiple deposition techniques. In one embodiment, as shown in FIG. 4C, the low-profile coating 344 can be deposited in a manner such that the distal end of the outer surface of the capillary 336 is not coated. In some embodiments, as shown in FIGS. 4D and 4E, the low-profile coating 344 can be deposited in a manner such that the distal end of the outer surface of the capillary 336 is coated. In FIG. 4E, the low-profile coating 344 can be deposited on at least a portion of the outer surface of the capillary 336 and on at least a portion of the outer surface of a buffer layer 330. In this example, the low-profile coating 344 may provide added mechanical strength to the interface between an optical fiber 314 and the capillary 336.

Figure 5A:
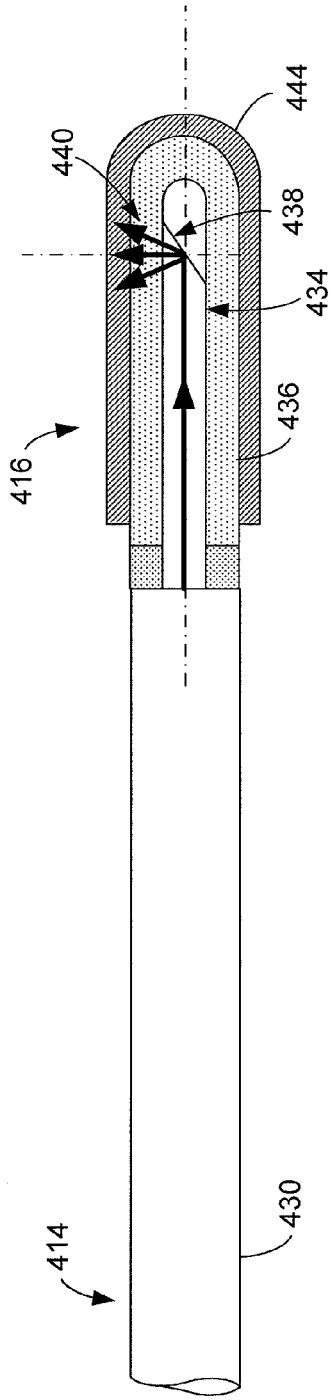
FIG. 5A is a cross-sectional view of a coated capillary with a light-sensitive portion of the coating exposed to laser energy according to an embodiment.
Figure 5B:
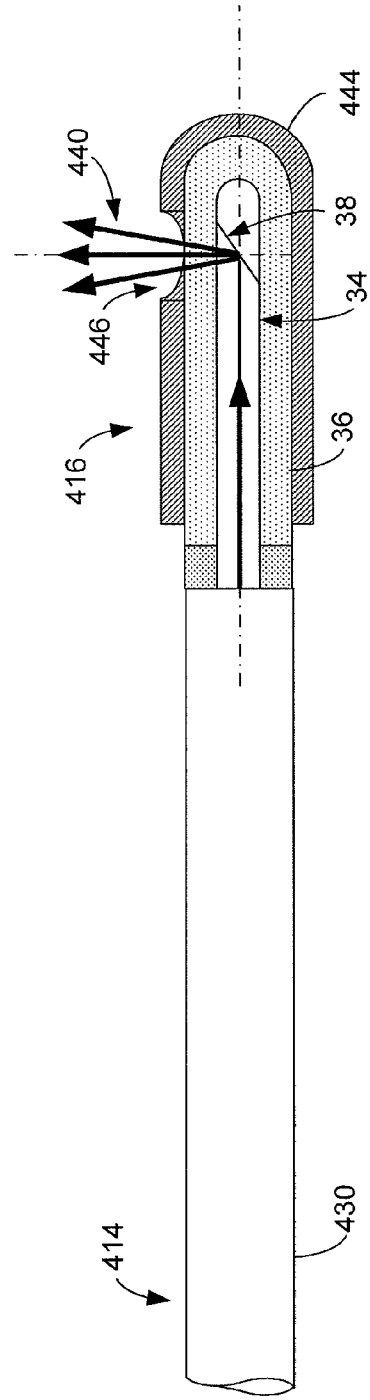
FIG. 5B is a cross-sectional view of a coated capillary with a light-sensitive portion of the coating removed after laser energy exposure according to an embodiment.

FIGS. 5A-5B illustrate a cross-sectional view of a capillary 436 with a portion of a low-profile coating 444 removed after exposure to laser energy, according to embodiments of the invention. After an optical-fiber distal end portion 416 is inserted into the endoscope 15 for use during a laser-based surgical procedure, a portion of the low-profile coating 444 can be removed or dissolved to provide an opening through which the side-fired or laterally-redirected laser energy can be transmitted. FIG. 5A shows a laser energy 440 being transmitted through an optical-fiber-core end portion 434 and being laterally redirected at a core-end angled surface 438 to the low-profile coating 444. The region of the low-profile coating 444 to which the laser energy 440 is redirected can be offset from a centerline or the longitudinal axis of the optical-fiber-core end portion 434. The light-sensitive material of the low-profile coating 444 can absorb the laser energy 440 to produce a change in the structural and/or chemical composition of the exposed material. As shown in FIG. 5B, the area or region from which the exposed material is removed can define an opening 446 through which the laser energy 440 can be transmitted. Exposure time sufficient to modify the light-sensitive material and produce the opening 446 may vary based on the material composition and properties. In one embodiment, a lumen within the endoscope can be used to supply a fluid or a gas to remove, dissolve, and/or collect the exposed material. Optionally, a separate medical device can be used to remove, dissolve, and/or collect the exposed material.

FIGS. 6A-6C illustrate a cross-sectional view of a capillary 536 with a low-profile sleeve 550, according to embodiments of the invention. The low-profile sleeve 550 can be disposed on at least a portion of an outer surface of the capillary 536 and/or the outer surface of a buffer layer 530. The low-profile sleeve 550 can slide or move relative to the capillary 536 and/or the buffer layer 530. The low-profile sleeve 550 can be made of various materials. For example, the low-profile sleeve 550 can be made of a material that is optically opaque to the laser energy that is used by the optical fiber side-firing system. In another example, the inner portion of the low-profile sleeve 550 can include a material having high lubridicity such that the inner portion of the low-profile sleeve 550 can easily slide or move relative to the capillary 536 and/or the buffer layer 530. In another example, the outer portion of the low-profile sleeve 550 can include a material such that the low-profile sleeve 550 provides appropriate protection to the capillary 536 during insertion into the endoscope and/or during operation of the optical fiber side-firing system. In another example, the low-profile sleeve 550 can include a material such that the low-profile sleeve 550 can provide added mechanical strength to the interface between an optical fiber 514 and the capillary 536.

As shown in FIG. 6A, the low-profile sleeve 550 can be disposed in a first position (e.g., have a first shape) when the distal end portion of the low-profile sleeve 550 covers the distal end portion of the outer surface of the capillary 536 but leaves the distal end or tip of the outer surface of the capillary 536 uncovered. FIG. 6B shows a different embodiment in which the distal end portion of the low-profile sleeve 550 covers the distal end portion of the outer surface of the capillary 536 while also covering a portion of the distal end or tip of the outer surface of the capillary 536. In FIG. 6C, the low-profile sleeve 550 can be disposed in a second or subsequent position (e.g., have a second or subsequent shape) when the distal end portion of the low-profile sleeve 550 does not cover the area or region in the distal end portion of the capillary 536 through which a laser energy 540 can be laterally transmitted during side-firing operations. A proximal end of the low-profile sleeve 550 can be pulled in a proximal direction to move or place the low-profile sleeve 550 into the second position. In some embodiments, after side-firing operations, the low-profile sleeve 550 can be placed back in the first position. In this regard, the proximal end of the low-profile sleeve 550 can be pushed in a distal direction to move or place the low-profile sleeve 550 back in the first position.

Figure 7A:
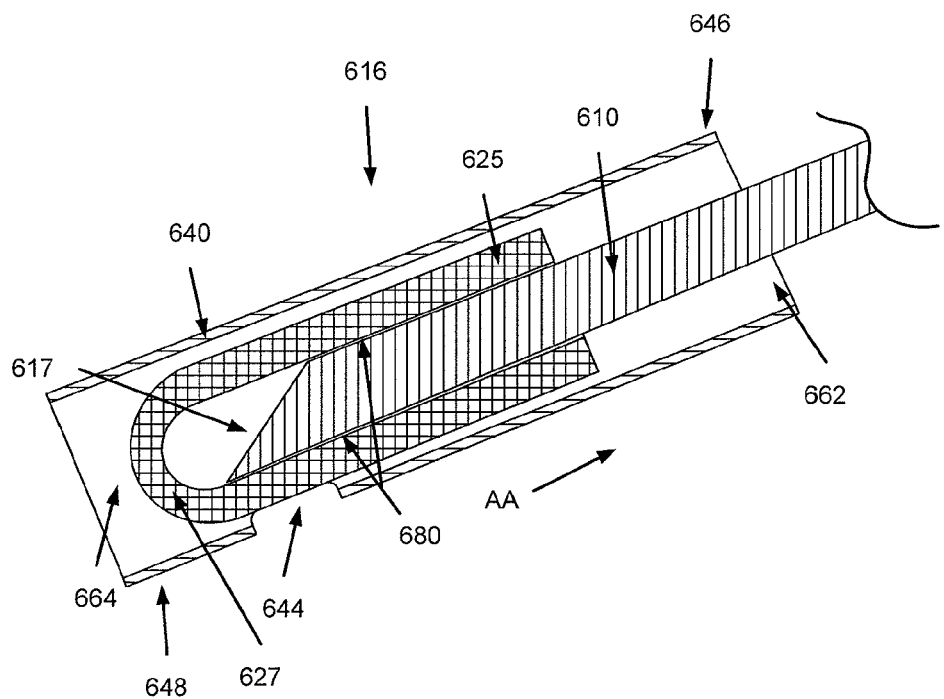
FIGS. 7A-7B are cross-sectional views of an optical-fiber distal end portion with a modifiable outer sleeve disposed around a capillary, according to an embodiment.
Figure 7B:
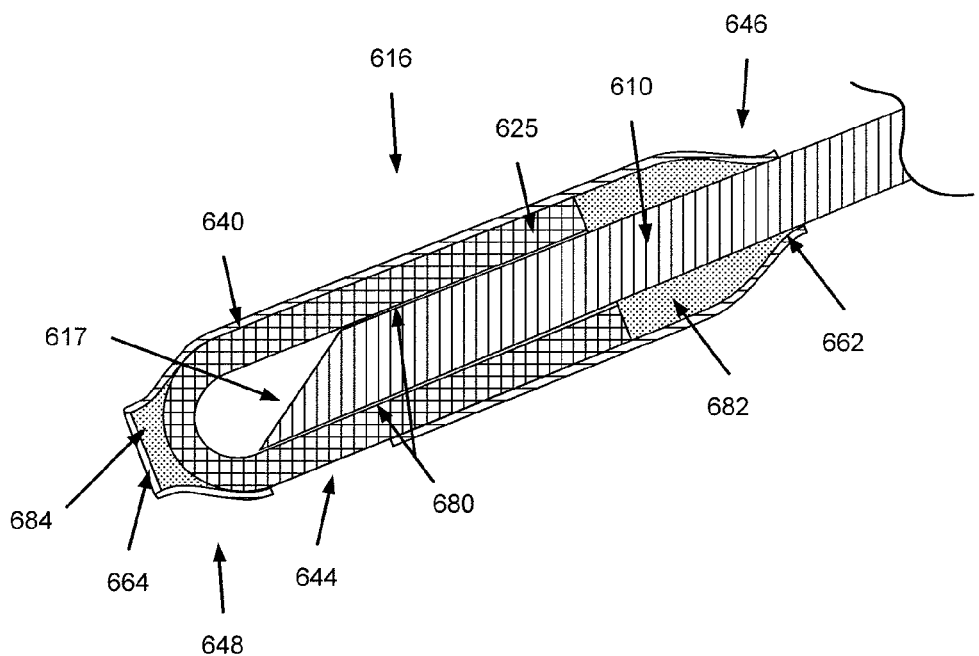

FIGS. 7A-7B are cross-sectional views of an optical-fiber distal end portion 616 with a modifiable outer sleeve 640 disposed around a capillary 625, according to an embodiment. Specifically, FIG. 7A illustrates the modifiable outer sleeve 640 in an expanded shape (also can be referred to an open shape), and FIG. 7B illustrates the modifiable outer sleeve 640 in a contracted shape (also can be referred to a closed shape or as a constricted shape). The modifiable outer sleeve 640 can be changed from the expanded shape (shown in FIG. 7A) to the contracted shape (shown in FIG. 7B) in response to, for example, an applied force, laser energy, and/or heat. In some embodiments, the modifiable outer sleeve can also be referred to as a cover or as a coating.

In some embodiments, the capillary 625 can be heat-fused and/or adhesively coupled at 680 to an optical fiber 610 of the optical-fiber distal end portion 616. As shown in FIG. 7A and FIG. 7B, an angled surface 617 is at a distal end of the optical fiber 610. The capillary 625 can be coupled to the optical fiber 610 after the angled surface 617 has been defined. Although not shown in FIG. 7A or FIG. 7B, the optical fiber 610 can have, for example, a fiber core, one or more cladding layers disposed around the fiber core, a buffer layer disposed around the cladding layer(s), and/or a jacket (disposed around the buffer layer).

As shown in FIG. 7A, the modifiable outer sleeve 640 defines a substantially straight tube with a constant (e.g., substantially constant) inner diameter when in the expanded shape. For example, an opening 664 at a distal end 648 of the modifiable outer sleeve 640 has substantially the same inner diameter as the entire the modifiable outer sleeve 640 (including an opening 662 at a proximal end 646 of the modifiable outer sleeve 640) when in the expanded shape. In some alternative embodiments, the modifiable outer sleeve 640 can have a different shape than a tube when in an expanded shape. For example, an alternative modifiable outer sleeve that has a tapered portion (e.g., a tapered distal end 648, a tapered proximal end 646) can be disposed around the capillary 625.

The modifiable outer sleeve 640 can be made of a material that changes from the expanded shape to the contracted shape when, for example, heat is applied. For example, the modifiable outer sleeve 640 can be made of a polymer-based material such as a tetrafluoroethylene (TFE) material, a polyaryletheretherketone (PEEK) material, and/or a nylon material that shrinks (e.g., contracts) when heated. When the modifiable outer sleeve 640 is in the contracted shape, the modifiable outer sleeve can function as a coating. In some embodiments, the modifiable outer sleeve 640 can include a mechanism that causes the modifiable outer sleeve 640 to change shape when, for example, actuated using an actuator. For example, the modifiable outer sleeve 640 can include a draw string that causes portions of the modifiable outer sleeve 640 to change from an expanded shape to a contracted shape around the capillary 625 and/or the optical fiber 610 when the draw string is pulled. In some embodiments, the modifiable outer sleeve 640 can be configured to change from the contracted shape and expanded shape, for example, when a forced is applied (e.g., when actuated) and/or when cooled.

The modifiable outer sleeve 640 can be disposed over the capillary 625 by moving the proximal end 646 of the modifiable outer sleeve 640 over a distal end 627 of the capillary 625 towards the angled surface 617 of the optical fiber 610 (shown as direction AA). The modifiable outer sleeve 640 can be moved until an opening 644 of the modifiable outer sleeve 640 is aligned over a portion of the capillary 625 through which laser energy redirected from the angled surface 617 will be transmitted. In some embodiments, the modifiable outer sleeve 640 can be moved over the capillary 625 into a desirable position over the capillary 625 from a direction opposite direction AA.

As shown in FIG. 7B, the modifiable outer sleeve 640 is constricted around the capillary 625 when in the contracted shape. The opening 664 of the modifiable outer sleeve 640 has a smaller inner diameter when in the contracted shape (shown in FIG. 7B) than the opening 664 of the modifiable outer sleeve 640 when in the expanded shape (shown in FIG. 7A). Similarly, when in the contracted shape, the opening 662 of the modifiable outer sleeve 640 has a smaller inner diameter (shown in FIG. 7B) than the opening 662 of the modifiable outer sleeve 640 when in the expanded shape (shown in FIG. 7A). In some embodiments, if the modifiable outer sleeve 640 is a heat-shrink material, the modifiable outer sleeve 640 can be changed to the contracted shape around the capillary 625 and/or the optical fiber 610 when (or after being) heated.

Although not shown, in some embodiments, the opening 644 can be produced after the modifiable outer sleeve 640 has been disposed around the capillary 625. For example, the opening 644 can be cut (e.g., cut using a cutting tool) from the modifiable outer sleeve 640 after the modifiable outer sleeve 640 is disposed over capillary 625 and when the modifiable outer sleeve 640 is in the expanded shape (such as the expanded shape shown in FIG. 7A). In some embodiments, for example, the opening 644 can be cut (e.g., cut using a cutting tool) from the modifiable outer sleeve 640 after the modifiable outer sleeve 640 is disposed over capillary 625 and when the modifiable outer sleeve 640 is in the contracted shape (such as the contracted shape shown in FIG. 7B).

Although not shown, in some embodiments, the opening 644 can be defined from at least a portion of the modifiable outer sleeve 640 that is made from a light-sensitive material. At least a portion of the opening 644 can be defined when the outer sleeve 640 is in the expanded shape (shown in FIG. 7A) and/or the contracted shape (shown in FIG. 7B). The light-sensitive material can be configured to, for example, absorb laser energy redirected from the angled surface 617 to produce a change in the structural and/or chemical composition of the light-sensitive material so that the opening 644 is defined. In some embodiments, substantially the entire modifiable outer sleeve 640 can be made from the light-sensitive material. More details related to defining an opening from a light-sensitive material are described above in connection with FIG. 5A.

In some embodiments, a portion distal to the capillary 625 can be filled with a material 684 and/or a portion proximal to the capillary 625 can be filled with a material 682. In some embodiments, the material 684 and/or the material 682 can be, for example, an adhesive (e.g., an epoxy), a polymer-based cap, a metal cap and/or so forth. In some embodiments, the material 684 can be moved (e.g., injected) through the opening 664 and into a position distal to the capillary 625 before and/or after the modifiable outer sleeve 640 is changed from the expanded shape to the contracted shape (via, for example, heating). Similarly, in some embodiments, the material 682 can be moved (e.g., injected) through the opening 662 and into a position proximal to the capillary 625 before and/or after the modifiable outer sleeve 640 is changed from the expanded shape to the contracted shape (via, for example, heating). In some embodiments, the material 682 and/or the material 684 can be coupled to (e.g., disposed on) the capillary 625 before the modifiable outer sleeve 640 is disposed over (and/or heat-shrunk on) the capillary 625.

In some alternative embodiments, the modifiable outer sleeve 640 can have a length that is different than that shown in FIG. 7A and/or FIG. 7B. For example, in some embodiments, the modifiable outer sleeve 640 can have a length that is equal to, or shorter than, a length of the capillary 625. In some embodiments, the modifiable outer sleeve 640 can be configured so that a circumferential portion (e.g., axial portion) of a distal portion of the capillary 625 and/or a circumferential portion (e.g., axial portion) of a proximal portion of the capillary 625 are exposed when the modifiable outer sleeve 640 is disposed over and/or coupled to (e.g., heat-shrunk to) the capillary 625.

In some embodiments, the capillary 625 can include one or more capillaries that are coupled together. In some embodiments, the capillaries included in the capillary 625 can be, for example, adhesively coupled to and/or heat-fused to one another. For example, a first capillary can be heat-fused to a cladding layer of the optical fiber 610. The first capillary can define at least a portion of an enclosure. A second capillary can be disposed outside of the first capillary and heat-fused to the first capillary. In some embodiments, the modifiable outer sleeve 640 can be coupled to an outer surface of the second capillary. Because the second capillary is disposed outside of the first capillary, the second capillary can be referred to as an outer capillary and the first capillary can be referred to as an inner capillary. When the capillary 625 includes more than one capillary, the capillary can be referred to as a multi-capillary.

In some embodiments, at least a portion of the capillary components and a distal end portion of the optical fiber can collectively define at least a portion of an angled surface. For example, at least a portion of an optical-fiber distal end portion can include a first capillary component disposed outside of and heat-fused during a first heat-fusing process to a distal portion of an optical fiber. Then, the first capillary component and the distal end portion of the optical fiber can be cleaved (and/or polished) to define an angled surface. Then a second capillary component disposed outside of the first capillary component can be heat-fused to the first capillary component during a second heat-fusing process. The angled surface can be defined after the first capillary component has been heat-fused to the optical fiber, so that a portion of the angled surface defined by the optical fiber can be defined as a substantially flat surface without, for example, being deformed (e.g., warped) during the first heat-fusing process. The first capillary component can function as a thermal insulator that protects the angled surface defined by the optical fiber during the second heat-fusing process. If instead the first capillary component was heat-fused to the distal end portion of the optical fiber after the distal end portion of the optical fiber has been cleaved (and polished), the heat-fusing could result in damage to the angled surface.

Figure 8:
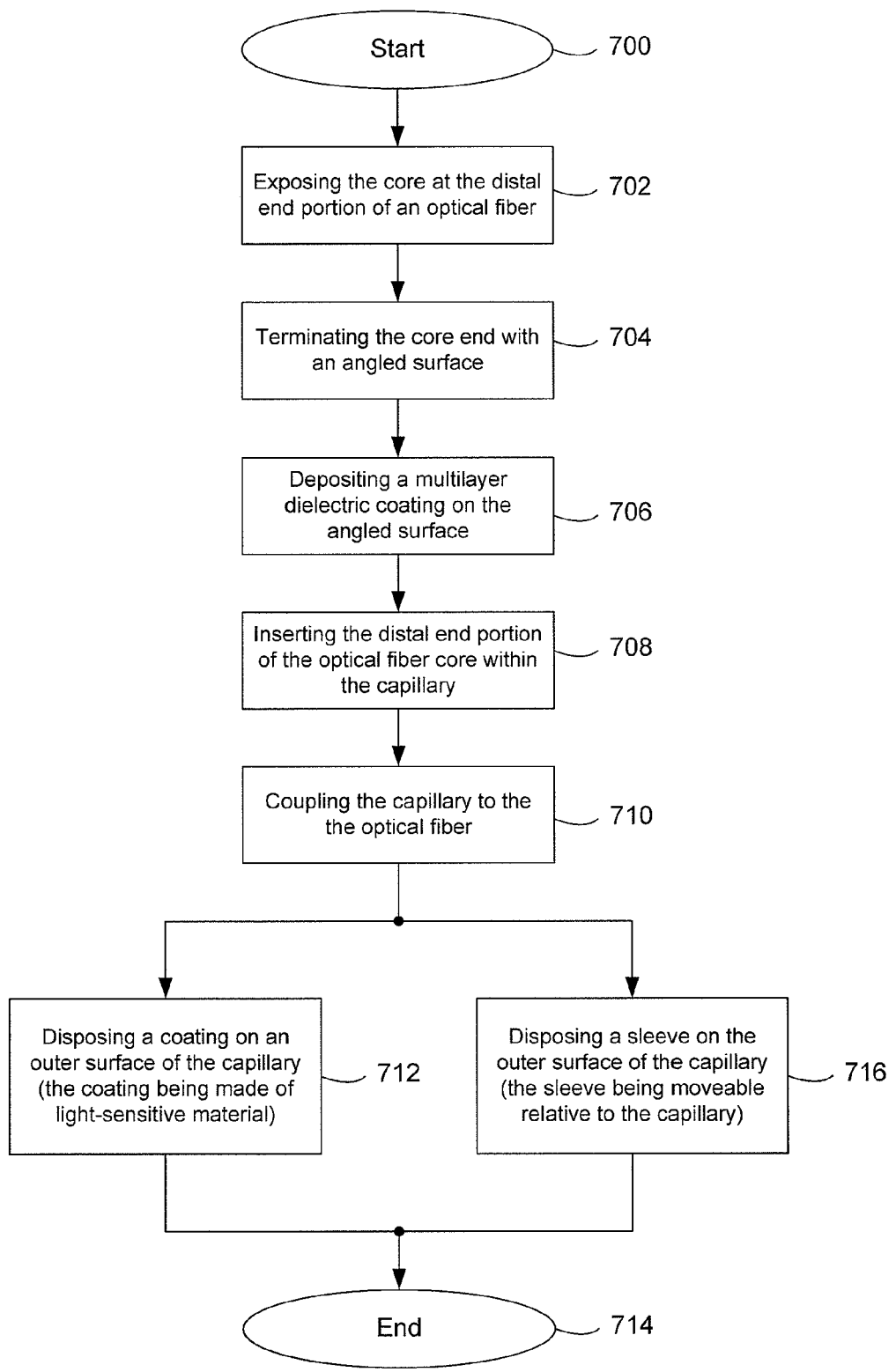
FIGS. 8-11 are flow charts illustrating a method according to an embodiment.

FIG. 8 is a flow chart illustrating a method for manufacturing a side-firing optical fiber, according to an embodiment of the invention. At 702, after start 700, a distal end portion of an optical fiber core can be exposed by removing a distal end portion of an optical fiber cladding and an optical fiber buffer from an optical fiber. At 704, the distal end portion of the optical fiber core can be terminated with an angled or beveled end surface. The angled end surface can be produced by cleaving and/or polishing the distal end surface of the optical fiber core. At 706, optionally, a reflecting coating, such as a multilayer dielectric coating, for example, can be deposited on the angled end surface to reduce the amount of laser energy that is not laterally redirected at the angled end surface but instead passes through the angled end surface in a direction substantially parallel to the longitudinal axis of the distal end portion of the optical fiber.

At 708, the exposed distal end portion of the optical fiber core can be disposed within an inner portion of a capillary. Optionally, a region that remains within the inner portion of the capillary after the disposing of the optical fiber core can be filled with a gas, a liquid, and/or a solid to improve the reflection at the angled end surface. At 710, a proximal end portion of the capillary can be coupled to the distal end portion of the optical fiber. In one example, the proximal end portion of the capillary and the distal end portion of the optical fiber can be fused together, which may result in an interface or fusion region.

In one embodiment, after 710, at 712, a low-profile cover can include a low-profile coating that can be deposited on the outer surface of the capillary and/or on the distal end portion of the buffer layer. The low-profile coating can be made of a light-sensitive material that can be removed or dissolved when exposed to laser energy. In another embodiment, the low-profile cover can include a low-profile sleeve that can be disposed (e.g., moved onto, deposited, heat shrunk) on the outer surface of the capillary and/or on the distal end portion of the optical fiber. The low-profile sleeve can move relative to the capillary and/or the distal end portion of the optical fiber. During manufacturing, the low-profile sleeve can be placed in a first position (e.g., a first shape) in which it can cover the distal end portion of the capillary. The low-profile sleeve can be moved into a second position (e.g., a second shape) in which the distal end portion of the capillary is exposed for side-firing operations during a laser-based surgical procedure. After 712 or 716, the method can proceed to end 714.

Figure 9:
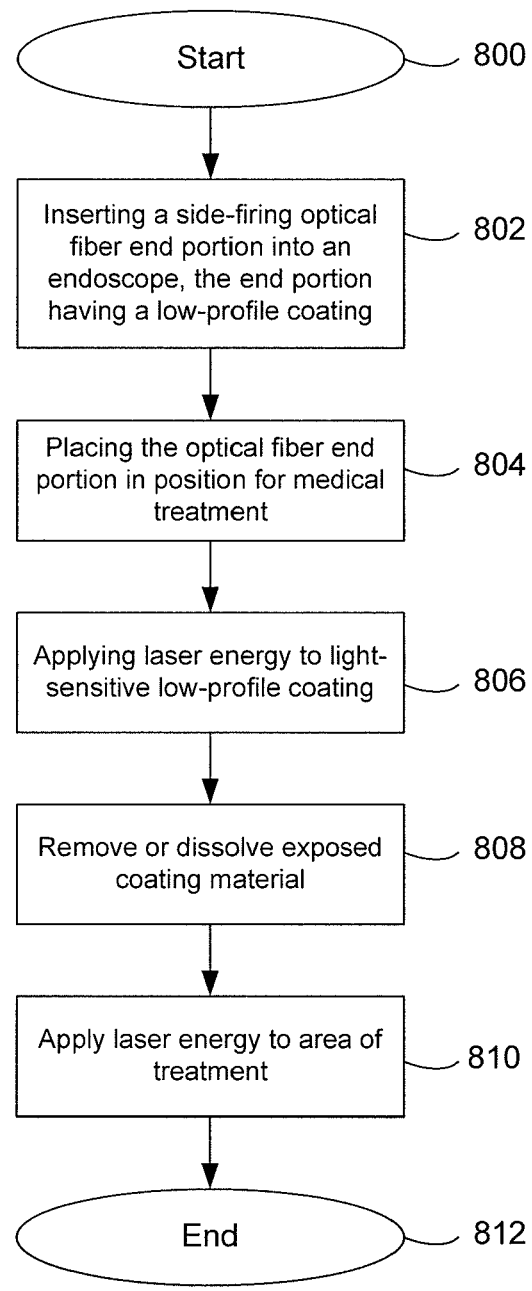

FIG. 9 is a flow chart illustrating a method of using an optical fiber side-firing system, according to another embodiment of the invention. At 802, after start 800, an optical-fiber distal end portion that includes a low-profile coating can be inserted within an inner portion or lumen of an endoscope. The low-profile coating can include a light-sensitive material. At 804, the endoscope can be at least partially inserted into the patient's body during a laser-based surgical procedure. Once inserted into the patient's body, the endoscope can be used to place or position the optical-fiber distal end portion at or near the area of treatment. At 806, laser energy from a laser source can be transmitted through the optical fiber such that laser energy is side-fired or laterally redirected at the optical-fiber distal end portion to expose the light-sensitive material in the low-profile coating. At 808, after sufficient exposure of the low-profile coating to the laser energy, the exposed material can be removed and/or dissolved to produce an opening or window through which laser energy can be transmitted. The endoscope can be used to remove and/or dissolve the exposed material. At 810, laser energy can be transmitted through the opening to provide laser treatment to the target area. After 810, the method can proceed to end 812.

Figure 10:
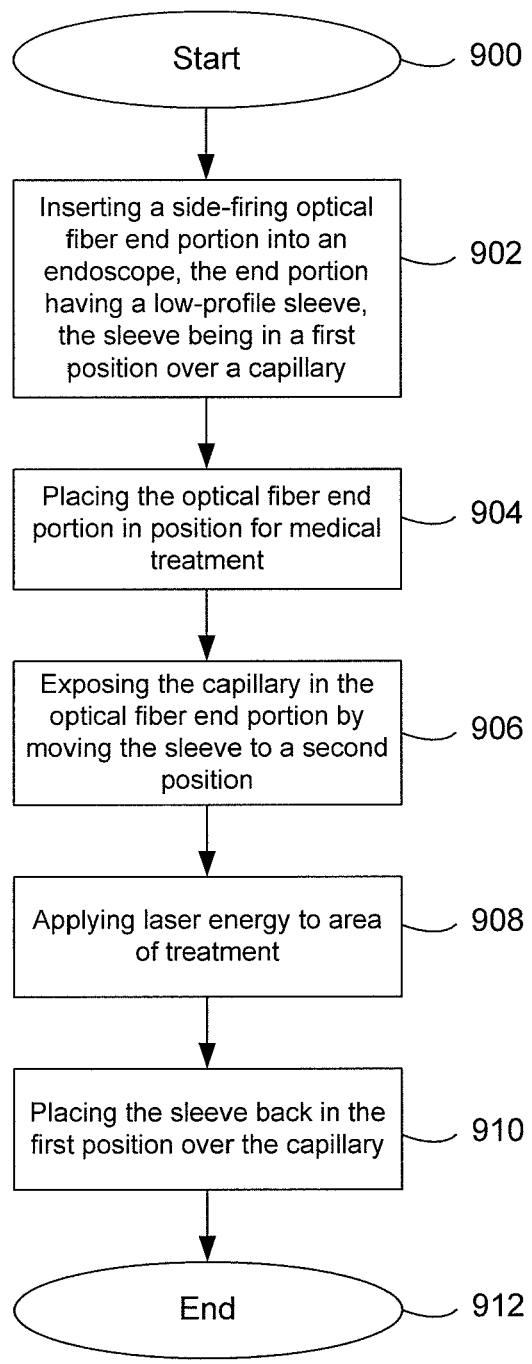

FIG. 10 is a flow chart illustrating a method of using an optical fiber side-firing system, according to another embodiment of the invention. At 902, after start 900, an optical-fiber distal end portion that includes a low-profile sleeve can be inserted within an inner portion or lumen of an endoscope. The low-profile sleeve can be positioned over a capillary when inserted into the endoscope. At 904, the endoscope can be at least partially inserted into the patient's body during a laser-based surgical procedure. Once inserted into the patient's body, the endoscope can be used to place or position the optical-fiber distal end portion at or near the area of treatment. At 906, the low-profile sleeve can be retracted or moved to a different position such that the capillary can be exposed to the area of treatment. At 908, laser energy from a laser source can be transmitted through the optical fiber such that laser energy is side-fired or laterally redirected at the optical-fiber distal end portion to treat the area of concern. At 910, optionally, the low-profile sleeve can be placed over the capillary during portions of the surgical procedure and/or at the end of the surgical procedure. After 910, the method can proceed to end 912.

Figure 11:
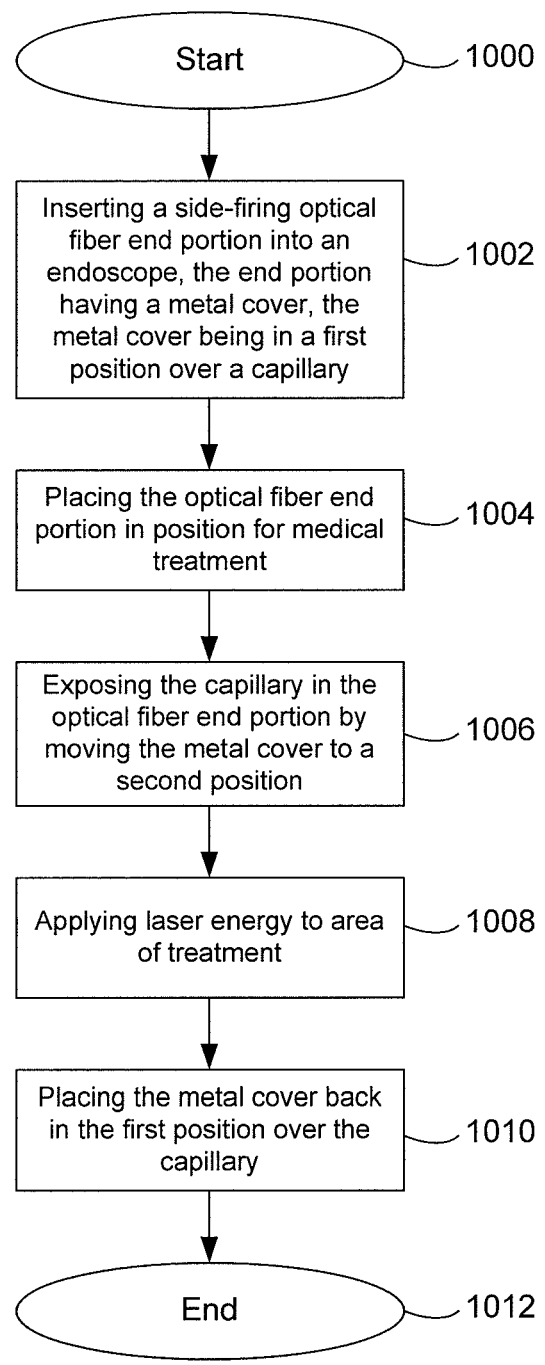

FIG. 11 is a flow chart illustrating a method of using an optical fiber side-firing system, according to another embodiment of the invention. At 1002, after start 1000, an optical-fiber distal end portion that includes a metal cover or cap can be inserted within an inner portion or lumen of an endoscope. The metal cover can be positioned over a capillary when inserted into the endoscope. At 1004, the endoscope can be at least partially inserted into the patient's body during a laser-based surgical procedure. Once inserted into the patient's body, the endoscope can be used to place or position the optical-fiber distal end portion at or near the area of treatment. At 1006, the metal cover can be retracted or moved to a different position such that the capillary can be exposed to the area of treatment. At 1008, laser energy from a laser source can be transmitted through the optical fiber such that laser energy is side-fired or laterally redirected at the optical-fiber distal end portion to treat the area of concern. At 1010, optionally, the metal cover can be placed over the capillary during portions of the surgical procedure and/or at the end of the surgical procedure. After 1010, the method can proceed to end 1012.

CONCLUSION

While various embodiments have been described above, it should be understood that they have been presented by way of example only, and not limitation. For example, the optical fiber side-firing system described herein can include various combinations and/or sub-combinations of the components and/or features of the different embodiments described. Although described with reference to use for treatment of symptoms related to BPH, it should be understood that the optical fiber side-firing system and the side-firing optical fibers, as well as the methods of using the optical fiber side-firing system and the side-firing optical fibers can be used in the treatment of other conditions.

Embodiments of a side-firing optical fiber can also be provided without the optical fiber side-firing system described herein. For example, a side-firing optical fiber can be configured to be used with other laser sources, endoscopes, etc., not specifically described herein. A side-firing optical fiber can have a variety of different shapes and sizes than as illustrated and described herein. A side-firing optical fiber can also include other features and/or components such as, for example, lenses and/or filters.

In one embodiment, an apparatus can include an optical fiber, a capillary, and a coating disposed on the capillary. The optical fiber can include a core. A proximal end portion of the optical fiber can be configured to be coupled to a laser source. A distal end of the core can include an angled surface relative to a longitudinal axis of a distal end portion of the core. The distal end of the core can be disposed within the capillary. A portion of the coating can be configured to be removed when exposed to transmitted laser energy from the distal end of the core. The angled surface of the distal end of the core can be configured to redirect laser energy in a lateral direction offset from the longitudinal axis. The coating can include a polymer and/or be biocompatible, for example.

The optical fiber can include a cladding disposed about at least a portion of the core and a buffer layer disposed about at least a portion of the cladding. The distal end of the core can be distal to a distal end of the cladding and to a distal end of the buffer layer. The apparatus can include a multilayer dielectric coating disposed on the angled surface of the core. The capillary can be coupled to a buffer layer of the optical fiber.

In another embodiment, an apparatus can include an optical fiber, a capillary, and a cover. The optical fiber can include a core. A distal end of the core can include an angled surface relative to a longitudinal axis of a distal end portion of the core. The distal end of the core can be disposed within the capillary. The cover can have a first position and a second position about the capillary. A distal end of the cover can be a distance of a distal end of the capillary when the cover is in its first position. The distal end of the cover can be a distance of the distal end of the capillary when the cover is in its second position. The distance when the cover is in the first position can be less than the distance when the cover is in the second position. The angled surface of the core can be configured to redirect laser energy in a lateral direction offset from the longitudinal axis. The cover can define a sleeve and/or be biocompatible.

The optical fiber can include a cladding disposed about at least a portion of the core and a buffer layer disposed about at least a portion of the cladding. The distal end of the core can be distal to a distal end of the cladding and to a distal end of the buffer layer. The apparatus can include a multilayer dielectric coating disposed on the angled surface of the core.

In another embodiment, a method can include exposing a distal end portion of a core from an optical fiber. A distal end of the core can include an angled surface relative to a longitudinal axis of the distal end portion of the core. The method can also include disposing the distal end of the core having the angled surface within a capillary. The capillary can include a coating disposed about at least a portion of an outer surface of the capillary. At least a portion of the coating can be configured to be removed when exposed to laser energy sent from the angled surface of the core.

In some instances, the method can include disposing the coating on the outer surface of the capillary. The method can include disposing a multilayer dielectric coating on the angled surface of the core, fixedly coupling the capillary and a buffer layer of the optical fiber together. Moreover, the method can include inserting the distal end portion of the core and the capillary into a patient's body after the disposing and, after the insertion, removing at least a portion of the coating.

In another embodiment, a method can include inserting a distal end portion of an optical fiber core and a capillary into a patient's body. The distal end of the optical fiber core can be disposed within the capillary. The distal end of the optical fiber core can include an angled surface. The capillary can include a coating disposed about at least a portion of an outer surface of the capillary. After the insertion, the method can include removing at least a portion of the coating. In some instances, the method can include exposing at least a portion of the coating to transmitted laser energy from the distal end of the optical fiber core after the insertion of the distal end portion of the optical fiber core and the capillary into the patient's body.

In another embodiment, a method can include disposing a cover on a capillary. The cover can have a first position and a second position about the capillary. A distal end of the cover can be a distance of a distal end of the capillary when the cover is in its first position and a distance of the distal end of the capillary when the cover is in its second position. The distance when the cover is in the first position can be less than the distance when the cover is in the second position. The cover can define a sleeve, for example. The method can include disposing a distal end of an optical fiber core within the capillary. The distal end of the optical fiber core can include an angled surface relative to a longitudinal axis of the distal end portion of the optical fiber core. In some instances, the method can include disposing a multilayer dielectric coating on the angled surface of the optical fiber core.

Moreover, the method can include inserting the distal end portion of the core and the capillary into a patient's body after disposing the cover on the capillary. The cover can be in the first position during the inserting. After the insertion, positioning the cover in the second position.

In another embodiment, an apparatus can include an optical fiber, a capillary, and a metal cover. The optical fiber can include a core. A distal end of the core can include a surface non-perpendicular to a longitudinal axis of a distal end portion of the core. The distal end of the core can be disposed within the capillary. The metal cover can have a first position and a second position about the capillary. A distal end of the metal cover can be a distance of a distal end of the capillary when the metal cover is in its first position and a distance of the distal end of the capillary when the metal cover is in its second position. The distance when the metal cover is in the first position can be less than the distance when the metal cover is in the second position.

The apparatus can include a protrusion coupled to a buffer layer of the optical fiber at a location. The protrusion can be configured to limit a distal end portion of the metal cover from sliding over the capillary in a proximal direction beyond the location of the protrusion. The apparatus can include an opening offset from the longitudinal axis. The opening can be at least partially aligned with a portion of the capillary through which laterally-redirected laser energy is transmitted when the metal cover is in the second position. In some instances, the apparatus can include a multilayer dielectric coating disposed on the distal end surface of the optical fiber core.

In another embodiment, a method can include inserting a distal end portion of a capillary into a patient's body. A distal end of an optical fiber core can be disposed within the capillary. A metal cover can be movably disposed about the capillary. The metal cover can have a first position and a second position with respect to the capillary. The metal cover can be in the first position during the inserting and after the inserting, the metal cover can be positioned in the second position. The method can include activating a laser source to transmit laser energy to the patient's body. The transmitted laser energy being laterally redirected at the distal end of the optical fiber core and passing through the capillary. In some instances, the method can include positioning the metal cover in the first position after the activating of the laser source is complete.

What is claimed is:

1. An apparatus, comprising: an optical fiber having a core, a proximal end portion of the optical fiber configured to be coupled to a laser source, a distal end of the core having an angled surface relative to a longitudinal axis of a distal end portion of the core; a capillary, the distal end of the core being disposed within the capillary; and a coating disposed on the capillary, a portion of the coating comprising a light-sensitive material configured to be removed when exposed to transmitted laser energy from the distal end of the core.

2. The apparatus of claim 1 wherein the optical fiber includes a cladding disposed about at least a portion of the core, and a buffer layer disposed about at least a portion of the cladding, the distal end of the core being distal to a distal end of the cladding and to a distal end of the buffer layer.

3. The apparatus of claim 1, further comprising a multi-layer dielectric coating disposed on the angled surface of the core.

4. The apparatus of claim 1, wherein the angled surface of the distal end of the core is configured to redirect laser energy in a lateral direction offset from the longitudinal axis.

5. The apparatus of claim 1, wherein the coating includes a polymer.

6. The apparatus of claim 1, wherein the coating is made from a heat-shrink material.

7. The apparatus of claim 1, wherein the capillary is coupled to a buffer layer of the optical fiber.

\* \* \* \* \*